United States Patent [19]

Grabner et al.

[11] Patent Number: 5,602,013
[45] Date of Patent: Feb. 11, 1997

[54] PROCESS FOR PRODUCING N-SUBSTITUTED-1-DEOXYNOJIRIMYCIN

[75] Inventors: Roy W. Grabner, Ballwin; Bryan H. Landis; Ping T. Wang, both of Manchester, all of Mo.; Michael L. Prunier, Vernon Hills; Mike G. Scaros, Arlington Heights, both of Ill.

[73] Assignee: G. D. Searle & Co., Chicago, Ill.

[21] Appl. No.: 444,636

[22] Filed: May 19, 1995

Related U.S. Application Data

[62] Division of Ser. No. 585,588, Sep. 20, 1990, abandoned.

[51] Int. Cl.$^6$ ............................. C12P 17/06; C12P 17/04; C12P 19/26
[52] U.S. Cl. ............................. 435/125; 435/84; 435/126
[58] Field of Search ............................. 435/84, 120, 122, 435/123, 126, 125

[56] References Cited

U.S. PATENT DOCUMENTS

| | | | |
|---|---|---|---|
| 3,956,337 | 5/1976 | Niwa et al. | 546/240 |
| 4,246,345 | 1/1981 | Kinast et al. | 435/84 |
| 4,266,025 | 5/1981 | Kinast et al. | 435/84 |
| 4,405,714 | 9/1983 | Kinast et al. | 435/84 |
| 4,611,058 | 9/1986 | Koebernick | 546/242 |
| 4,806,650 | 2/1989 | Schröder et al. | 546/242 |
| 4,940,705 | 7/1990 | Böshagen et al. | 546/242 |

OTHER PUBLICATIONS

Kagan et al. The Preparation of Glycamines, J. Amer. Chem. Soc. 79:3541 (1957).

Mitts, Eleanor and Hixon, R. M. The Reaction of Glucose With Some Amines. J. Amer. Chem. Soc. 66:483 (1944).

Mohammed A. and Olcott, Harold S. Relative Stabilities of D–Glucose Amine Derivatives. J. Amer. Chem. 66:969 (1947).

Rylander, Paul N. Hydrogenation Methods. Academic Press (1985) pp. 82–93.

White, S. A. and Claus, G. W. Effect of Intracytoplasmic Membrane Development on Oxidation of Sorbitol and Other Polyols by *Gluconobacter oxydans*. J. of Bacteriology 150:934–943 (1982).

Green In Protective Gaps in Organic Synthesis, John Urley and Son, pp. 272–273, 19181.

Jones J K N et al, Can. J. Chem. 39: 2400–10 (1961).

Jones J B, Tetrahedron 42:3351–3403 (1986).

*Primary Examiner*—Irene Marx
*Assistant Examiner*—S. Saucier
*Attorney, Agent, or Firm*—Fitzpatrick, Cella, Harper & Scinto

[57] ABSTRACT

The invention is a process for producing N-substituted glucamines, a process for oxidizing an N-substituted glucamine with an oxidizing microbe or extract thereof, and a process for oxidizing an N-substituted glucamine with an oxidizing microbe or extract thereof and reducing the oxidized N-substituted glucamine to an N-substituted-1-deoxynojirimycin. In addition, a one pot process for producing N-substituted-1-deoxynojirimycin from D-glucose is disclosed.

14 Claims, No Drawings

PROCESS FOR PRODUCING N-SUBSTITUTED-1-DEOXYNOJIRIMYCIN

This is a DIVISIONAL, Application of application Ser. No. 07/585,588 filed on Sep. 20, 1990 now abandoned.

FIELD OF THE INVENTION

This invention relates to a process for production of N-substituted-1-deoxynojirimycin and intermediates for its production.

BACKGROUND OF THE INVENTION

A process for the preparation of 1-deoxynojirimycin in which 1-aminosorbitol is oxidized microbiologically to give 6-aminosorbose, which is then hydrogenated with a catalyst to give 1-deoxynojirimycin is disclosed in U.S. Pat. No. 4,246,345. However, the yields of this process, in particular the low volume yields in the microbiological reaction are related to degradation problems and short reaction times, in addition no process for production of N-substituted derivatives of 1-deoxynojirimycin is disclosed.

It is known that N-substituted derivatives of 1-deoxynojirimycin can be made by protecting aminosorbitols with protecting groups which are stable in subsequent microbial oxidations. The protecting groups can subsequently be removed by catalytic hydrogenation. Such a process is disclosed in U.S. Pat. No. 4,266,025. In the '025 patent, protected amino sugars are oxidized microbiologically to give protected 6-aminosorboses, which are then isolated. The protective group is then removed by catalytic hydrogenation and the ring is reclosed to form the N-substituted derivatives of 1-deoxynojirimycin. However, the '025 process requires a large amount of catalyst in the hydrogenation step. In addition, the unprotected 6-aminosorboses cannot be isolated as such.

U.S. Pat. No. 4,405,714 discloses a process for producing N-substituted derivatives of 1-deoxynojirimycin in which glucose is converted into a 1-aminosorbitol, the 1-aminosorbitol is then protected by a protecting group which is stable in the subsequent microbiological oxidation process. The protecting group can then be removed under acid conditions. The compounds are oxidized microbially to give a protected 6-aminosorbose. The protective group on the 6-aminosorbose is then removed under acid conditions. The 6-aminosorbose salt thus obtained is hydrogenated with a catalyst to give the N-substituted derivative of 1-deoxynojirimycin. The '714 process, like the '025 process, requires the use of protective groups to obtain N-substituted derivatives of 1-deoxynojirimycin.

It has been discovered that N-substituted derivatives of 1-deoxynojirimycin can be made by a process which does not require the use of protecting groups.

SUMMARY OF THE INVENTION

This invention is a process which comprises oxidizing a glucamine of the formula:

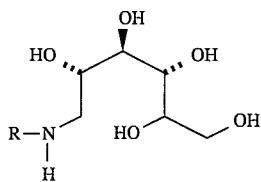
(I)

or salts thereof, with an oxidizing microbe or extract thereof, and producing compounds of the formula:

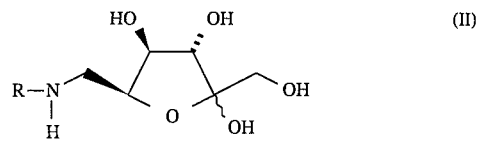
(II)

or salts thereof, in which R, in each instance, is phenyl, $C_1$–$C_{10}$ alkyl, $C_1$–$C_{10}$ alkyl substituted with phenyl or carboxy, or $C_2$–$C_{10}$ alkyl substituted with hydroxy.

In one embodiment of the invention, a 6-(substituted amino)-6-deoxy-α-L-sorbofuranose produced by the above described reaction is reduced (with or without isolation of the intermediate sorbose) to N-substituted-1-deoxynojirimycin, or salts thereof, of formula III (shown below).

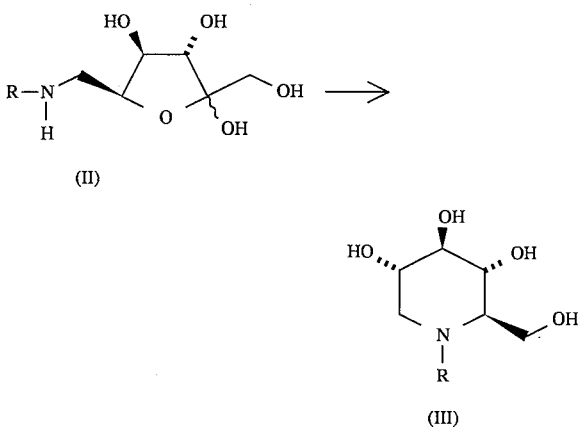

wherein R is the same as described above.

In another embodiment of the invention, D-glucose is converted to N-substituted-1-deoxynojirimycin in a one pot process:

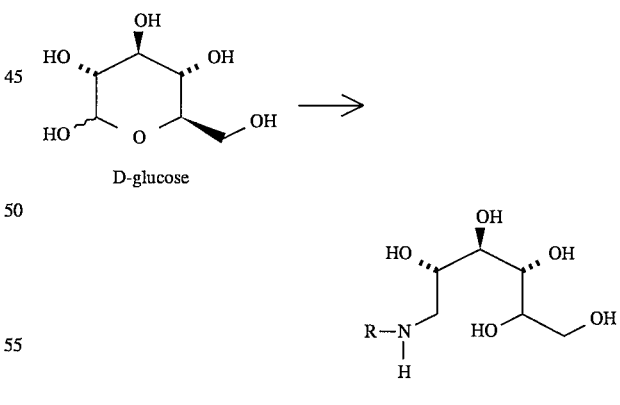

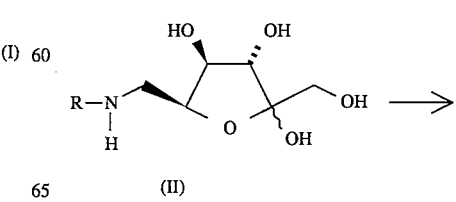
(II)

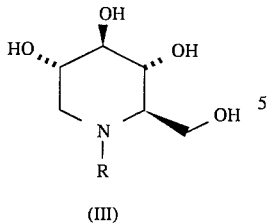

(III)

Another embodiment of the invention is a process for producing N-substituted glucamines and salts thereof.

In another embodient, the compound 6-butylamino-6-deoxy-α-L-sorbofuranose and salts thereof are disclosed.

The exact form of the structure of formula II is dictated by the environment in which the sorbose is present (See H. Paulsen et al., *Chem. Ber.* 100:802 (1967)). The use of the sorbofuranose or the sorbose nomenclature is not meant to imply that the compound cannot or does not exist in another of its equivalent forms.

The 6-(substituted amino)-6-deoxy-α-L-sorbofuranose produced by the microbial oxidation of N-substituted glucamines are useful as intermediates for producing N-substituted-1-deoxynojirimycin compounds (which are antiviral agents, antidiuretics, antidiabetics, animal feed additives and antihyperglycemics).

As used herein, the glucamines of the above formula I are referred to as "N-substituted glucamines" (also known as 1-(substituted amino)-1-deoxy-D-glucitol). The compounds of the above formula II are hereinafter referred to as "6-substituted amino-6-deoxy-α-L-sorbofuranoses". The compounds of the above formula III are referred to as "N-substituted-1-deoxynojirimycins"(also known as 1,5-(substituted imino)-1,5-dideoxy-D-glucitol and 1-substituted-3,4,5-trihydroxy-2-piperidinylmethanol.)

Straight chain or branched chain alkyls are suitable to practice the process of the invention, with $C_1$–$C_5$ alkyl groups preferred. Examples of suitable alkyl radicals are methyl, ethyl, n-propyl, 1-methylethyl, n-butyl, 1-methylpropyl, 1,1-dimethylethyl, n-pentyl, 3-methylbutyl, 1-methylbutyl, 2-methylbutyl, n-hexyl, n-heptyl, n-octyl, n-nonyl and n-decyl. Suitable hydroxy substituted alkyl radicals are 2-hydroxyethyl, 3-hydroxypropyl, 4-hydroxybutyl, 5-hydroxypentyl, 6-hydroxyhexyl, 7-hydroxyheptyl, 8-hydroxyoctyl, 9-hydroxynonyl, and 10-hydroxydecyl. Suitable carboxy substituted alkyl radicals are carboxymethyl, 2-carboxyethyl, 3-carboxypropyl, 4-carboxybutyl, 5-carboxypentyl, 6-carboxyhexyl, 7-carboxyheptyl, 8-carboxyoctyl, 9-carboxynonyl and 10-carboxydecyl. Suitable phenyl substituted alkyl radicals are phenylmethyl (benzyl), 2-phenylethyl, 3-phenylpropyl, 4-phenylbutyl, 5-phenylpentyl, 6-phenylhexyl, 7-phenylheptyl, 8-phenyloctyl, 9-phenylnonyl and 10-phenyldecyl. Phenyl alone is also an acceptable radical.

Examples of 6-substituted amino-6-deoxy-α-L-sorbofuranoses which are produced by the process of the invention are:

6-methylamino-6-deoxy-α-L-sorbofuranose, 6-ethylamino-6-deoxy-α-L-sorbofuranose, 6-n-propylamino-6-deoxy-α-L-sorbofuranose, 6-(1-methylethyl)amino-6-deoxy-α-L-sorbofuranose, 6-n-butylamino-6-deoxy-a-L-sorbofuranose, 6-(1-methylpropyl)amino-6-deoxy-α-L-sorbofuranose, 6-(1,1-dimethylethyl)amino-6-deoxy-α-L-sorbofuranose, 6-n-pentylamino-6-deoxy-α-L-sorbofuranose, 6-(3-methylbutyl)amino-6-deoxy-α-L-sorbofuranose, 6-(1-methylbutyl)amino-6-deoxy-α-L-sorbofuranose, 6-(2-methylbutyl)amino-6-deoxy-α-L-sorbofuranose, 6-n-hexylamino-6-deoxy-α-L-sorbofuranose, 6-n-heptylamino-6-deoxy-α-L-sorbofuranose, 6-n-octylamino-6-deoxy-α-L-sorbofuranose, 6-n-nonylamino-6-deoxy-α-L-sorbofuranose, 6-n-decylamino-6-deoxy-α-L-sorbofuranose, 6-(2-hydroxyethyl)amino-6-deoxy-α-L-sorbofuranose, 6-(3-hydroxypropyl)amino-6-deoxy-α-L-sorbofuranose, 6-(4-hydroxybutyl)amino-6-deoxy-α-L-sorbofuranose, 6-(5-hydroxypentyl)amino-6-deoxy-α-L-sorbofuranose, 6-(6-hydroxyhexyl)amino-6-deoxy-α- L-sorbofuranose, 6-(7-hydroxyheptyl)amino-6-deoxy-α-L-sorbofuranose, 6-(8-hydroxyoctyl)amino-6-deoxy-α-L-sorbofuranose,, 6-(9-hydroxynonyl)amino-6-deoxy-α-L-sorbofuranose, 6-(10-hydroxydecyl)amino-6-deoxy-α-L-sorbofuranose, 6-(carboxymethyl)amino-6-deoxy-α-L-sorbofuranose, 6-(2-carboxyethyl)amino-6-deoxy-α-L-sorbofuranose, 6-(3-carboxypropyl)amino-6-deoxy-α-L-sorbofuranose, 6-(4-carboxybutyl)amino-6-deoxy-α-L-sorbofuranose, 6-(5-carboxypentyl)amino-6-deoxy-α-L-sorbofuranose, 6-(6-carboxyhexy)amino-6-deoxy-α-L-sorbofuranose, 6-(7-carboxyheptyl)amino-6-deoxy-α-L-sorbofuranose, 6-(8-carboxyoctyl)amino-6-deoxy-α-L-sorbofuranose, 6-(9-carboxynonyl)amino-6-deoxy-α-L-sorbofuranose, 6-(10-carboxydecyl)amino-6-deoxy-α-L-sorbofuranose, 6-phenylamino-6-deoxy-α-L-sorbofuranose, 6-(phenylmethyl)amino-6-deoxy-α-L-sorbofuranose, 6-(2-phenylethyl)amino-6-deoxy-α-L-sorbofuranose, 6-(3-phenylpropyl)amino -6-deoxy-α-L-sorbofuranose, 6-(4-phenylbutyl)amino-6-deoxy-α-L-sorbofuranose, 6-(5-phenylpentyl)amino-6-deoxy-α-L-sorbofuranose, 6-(6-phenylhexyl)amino-6-deoxy-α-L-sorbofuranose, 6-(7-phenylheptyl)amino-6-deoxy-α-L-sorbofuranose, 6-(8- phenyloctyl)amino-6-deoxy-α-L-sorbofuranose, 6-(9-phenylnonyl)amino-6-deoxy-α-L-sorbofuranose, and 6-(10-phenyldecyl)amino-6-deoxy-α-L-sorbofuranose.

N-substituted glucamines of formula I can be obtained by known means, for example, by amination of D-glucose. The reductive alkylation of sugars with amines is reported in the literature as a method for preparing N-substituted1-amino-1-deoxy sugars (see F. Kagan et al., *J. Amer. Chem. Soc,* 79, 3541 (1957), A. Mohammad et al., *J. Am. Chem. Soc.*, 66,969 (1947), P. N. Rylander, *Hydrogenation Methods* (Academic Press, (1985) pp. 82–93) and G. Mitts et al., *J. Am. Chem. Soc.* 66:483 (1944)). In general these preparations involve reacting a sugar and an amine, in varying ratios, in a suitable solvent such as aqueous methanol or ethanol. A catalytic amount of hydrochloric acid is sometimes added. The resulting mixture is hydrogenated under 40–1300 psig of hydrogen pressure at 23°–100° C. for 7–30 hours. The resulting 1-(substituted amino)1-deoxy D-glucitol (N-substituted glucamine) is then isolated.

In a preferred process for preparing N-substituted glucamine salts, a Parr shaker bottle, or the like, is charged with a solvent and amine. Suitable solvents include water, alcohols (such as methanol and ethanol) or aqueous alcohols. Preferably the solvent is ethanol. Suitable amines include but are not limited to the amines described for preparing the N-substituted glucamines described for formulas I, II, and III. Preferred amines include ethylamine, n-butylamine, n-octylamine, 2-hydroxyethylamine, phenylmethylamine, phenylamine and 4-carboxybutylamine. The ratio of D-glucose to amine is about 1:1, which allows the product to be used without isolation or removal of excess reagents. The mixture is stirred and cooled while acid is slowly added until a pH in the range of about 8.0 to 12.0 is obtained, preferably about 9 to 10.5. Suitable acids include hydrochloric acid, sulphuric acid, nitric acid, acetic acid, ascorbic acid, succinic acid, citric acid, maleic acid, oxalic acid, and phosphoric acid, preferably hydrochloric acid. To the Parr shaker bottle is added D-glucose followed by palladium-on-carbon (Pd/C) catalyst (50% water-wet). A palladium catalyst loading of about 1% to 50% by weight glucose is used, preferably about 10% to 30%. Catalysts from the noble metals can be used, for example, platinum, palladium, rhodium and rhenium, preferably palladium. The mixture is agitated and hydrogenated at a pressure of about 1 to 100 atm, preferably about 3–6 atm of hydrogen at a temperature of about 25° C. to 100° C., preferably about 40° C. to 80° C., until the reaction is complete (as indicated by hydrogen uptake). The hydrogen is vented and the palladium-on-carbon removed by filtration (preferably through a layer of powdered cellulose). The catalyst is washed with solvent such as an alcohol, preferably ethanol, followed by washing with water. The washes are combined with the filtrate to give a solution containing a mixture of N-substituted glucamine and its corresponding salt. The mixture is stirred and cooled while hydrochloric add is slowly added to a final pH of about 1 to 7, preferably about 4 to 6. The ethanol is removed by distillation under reduced pressure. The residue contains the N-substituted glucamine salt. The residue is diluted with water and ready to use in the next step of microbial oxidation without purification. Thus, the process produces the N-substituted glucamine salts from D-glucose without isolation or removal of excess reagents. The elimination of isolation and excess reagent removal steps allows for the direct use of N-substituted glucamines in the microbial oxidation, which oxidation results in the 6-substituted amino-6-deoxy-α-L-sorbofuranoses which in turn can be directly hydrogenated to N-substituted-1-deoxynojirimycins (i.e. one pot process).

An additional advantage of the N-substituted glucamine salts is the elimination of odor associated with residual amines. Typically the amines are extremely odoriferous, requiring the use of respirators when handling. On the other hand, the glucamine salts are relatively odor free, which enables handling without special precautions such as respirators.

As indicated by Material Safety Data Sheets from suppliers of N-n-butylamine (Fisher Scientific, Fair Lawn, N.J., for example), the N-n-butylamine compound is toxic and a severe eye, skin and mucous membrane irritant. Exposure to as little as 5–10 ppm of N-butylamine produces nose and throat irritation. Exposure to concentrations of 10–25 ppm are intolerable for more than a few minutes. Thus, the salt forms of the N-substituted glucamine compounds, which forms do not have the odor and irritation characteristics of the non-salt forms are advantageous.

To begin the microbial oxidation of an N-substituted glucamine, oxidizing microorganisms are added to a reaction mixture which comprises an N-substituted glucamine or salts thereof. Alternatively, N-substituted glucamine or a salt thereof is added to cultures of oxidizing microorganisms that will carry out the oxidation step. Preferably a salt of N-substituted glucamine is added. Suitable salts of N-substituted glucamine include but are not limited to salts of chloride, sulphate, nitrate, acetate, ascorbate, succinate, citrate, maleate, oxalate, or phosphate. Preferably the hydrochloride salt is used. Although the use of a salt is preferred, a salt can be made in situ by the addition of an N-substituted glucamine and suitable acids to lower the pH and create an N-substituted glucamine salt. During incubation of the reaction mixture containing microorganisms, the reaction is monitored with a reverse phase or ion exchange high performance liquid chromatography (HPLC) assay to observe conversion of N-substituted glucamine to the respective 6-(substituted amino)-6-deoxy-α-L-sorbofuranose. Thin layer chromatography (TLC) and gas chromatography (GC) can also be used to monitor the conversion.

Oxidizing microorganisms which are suitable for carrying out the oxidation (or microorganisms from which active extracts for carrying out the oxidation are obtained) can be Procaryotae (bacteria), or Eucaryotae, for example fungi, which in each case can belong to diverse taxonomic groups. Suitable microorganisms are found by growing a relatively large number of microorganisms in an appropriate nutrient medium which contains sorbitol or N-substituted glucamines and examining their ability to produce sorbose or 6-(substituted amino)-6-deoxy-α-L-sorbofuranoses, respectively. The ability of a microorganism to catalyze the oxidation reaction according to the invention can be measured by a variety of means, including assaying with high performance liquid chromatography (HPLC). Microorganisms for use in the process of the invention are readily available from a variety of sources including but not limited to the American Type Culture Collection (ATCC), Rockville, Md.; the Agricultural Research Culture Collection (NRRL), Peoria, Ill.; Deutsche Sammlung Von Mikroorganismen (DSM), Federal Republic of Germany; and the Fermentation Research Institute (FRI), Japan.

Examples of suitable oxidizing microorganisms are bacteria from the order Pseudomonadales, bacteria from the family Pseudomonadaceae, bacteria from the family Coryneform, and fungi from the genus Metschnikowia. Within the Pseudomonadales order, preference is for representatives of the family Pseudomonadaceae. Within the Pseudomonadaceae family, bacteria of the genus Gluconobacter (formerly called Acetobacter) are preferred. Bacteria from the group of Coryneform bacteria, in particular those of the genus Corynebacterium (also known as Curtobacterium), are also suitable. Finally, the oxidation can be carried out with fungi (for example, with yeasts) in particular with those of the family Spermophthoraceae, such as the genus Metschnikowia.

Examples of suitable Corynebacterium are *Corynebacterium acetoacidophilum, Corynebacterium acetoglutamicum, Corynebacterium acnes, Corynebacterium alkanolyticum, Corynebacterium alkanum, Corynebacterium betae, Corynebacterium bovis, Corynebacterium callunae, Corynebacterium cystitidis, Corynebacterium dioxydans, Corynebacterium equi, Corynebacterium flavescens, Corynebacterium glutamicum, Corynebacterium herculis, Corynebacterium hoagii, Corynebacterium hydrocarbooxydans, Corynebacterium ilicis, Corynebacterium lilium, Corynebacterium liquefaciens, Corynebacterium matruchotii, Corynebacterium melassecola, Corynebacterium mycetoides, Corynebacterium nephridii, Corynebacterium nitrilophilus, Corynebacterium oortii, Corynebacterium petrophilum, Corynebacterium pilosum, Corynebacterium pyogenes, Corynebacterium rathayi, Corynebacterium renale, Corynebacterium simplex, Corynebacterium striatum, Corynebacterium tritici, Corynebacterium uratoxidans, Corynebacterium vitarumen,* and *Corynebacterium*

*xerosis*. Suitable Gluconobacterium for use in the process of the invention include *Gluconobacter oxydans* subsp. *industrius*, *Gluconobacter oxydans* subsp. *melanogenes*, *Gluconobacter oxydans* subsp. *sphaericus*, and *Gluconobacter oxydans* subsp. *suboxydans*. Metschnikowia (formerly called Candida) preferred for use in the process of the invention include *Metschnikowia pulcherrimia*.

General growth conditions for culturing the particular organisms are obtained from depositories and from texts known in the art such as Bergey's Manual of Systematic Bacteriology, Vol. 1, Williams and Wilkins, Baltimore/London (1984), N. R. Krieg, ed.

The nutrient medium for the growth of any oxidizing microorganism should contain sources of assimilable carbon and nitrogen, as well as mineral salt. Suitable sources of assimilable carbon and nitrogen include, but are not limited to, complex mixtures, such as those constituted by biological products of diverse origin, for example soy bean flour, cotton seed flour, lentil flour, pea flour, soluble and insoluble vegetable proteins, corn steep liquor, yeast extract, peptones and meat extracts. Additional sources of nitrogen are ammonium salts and nitrates, such as ammonium chloride, ammonium sulphate, sodium nitrate and potassium nitrate. Generally, the nutrient medium should include, but is not limited to, the following ions: $Mg^{++}$, $Na^+$, $K^+$, $Ca^{++}$, $NH_4^+$. $Cl^-$, $SO_4^{--}$, $PO_4^{---}$ and $NO_3^-$ and also ions of the trace elements such as Cu, Fe, Mn, Mo, Zn, Co and Ni. The preferred source of these ions are mineral salts.

If these salts and trace elements are not present in sufficient amounts in the complex constituents of the nutrient medium or in the water used it is appropriate to supplement the nutrient medium accordingly.

The microorganism employed in the process of the invention can be in the form of fermentation broths, whole washed cells, concentrated cell suspensions, enzyme extracts, and immobilized cells. Preferably concentrated cell suspensions, enzyme extracts, and whole washed cells are used with the process of the invention (S. A. White and G. W. Claus (1982), J. Bacteriology 150:934–943).

Concentrated washed cell suspensions may be prepared as follows: The microorganisms are cultured in a suitable nutrient solution, harvested (for example by centrifuging) and suspended in a smaller volume (in salt or buffer solutions, such as physiological sodium chloride solution or aqueous solutions of potassium phosphate, sodium acetate, sodium maleate, magnesium sulfate, or simply in tap water, distilled water or nutrient solutions). N-substituted glucamine or a salt thereof is then added to a cell suspension of this type and the oxidation reaction according to the invention is carried out under the conditions described.

The conditions for oxidation of N-substituted glucamine in growing microorganism cultures or fractionated cell extracts are advantageous for carrying out the process according to the invention with concentrated cell suspensions. In particular the temperature range is from about 0° C. to about 45° C. and the pH range is from about 2 to about 10. There are no special nutrients necessary in the process of the invention. More importantly, washed or immobilized cells can simply be added to a solution of N-substituted glucamine or salts thereof, without any nutrient medium present.

It is also possible to carry out the process according to the invention with enzyme extracts or enzyme extract fractions prepared from bacteria. The extracts can be crude extracts, such as obtained by conventional digestion of microorganism cells. Methods to break up cells include, but are not limited to, mechanical disruption, physical disruption, chemical disruption, and enzymatic disruption. Such means to break up cells include ultrasonic treatments, passages through French pressure cells, grindings with quartz sand, autolysis, heating, osmotic shock, alkali treatment, detergents, or repeated freezing and thawing.

If the process according to the invention is to be carried out with partially purified enzyme extract preparations, the methods of protein chemistry, such as ultracentrifuging, precipitation reactions, ion exchange chromatography or adsorption chromatography, gel filtration or electrophoretic methods, can be employed to obtain such preparations. In order to carry out the reaction according to the invention with fractionated cell extracts, it may be necessary to add to the assay system additional reactants such as, physiological or synthetic electron acceptors, like NAD+, NADP+, methylene blue, dichlorophenolindophenol, tetrazolium salts and the like. When these reactants are used, they can be employed either in equimolar amounts (concentrations which correspond to that of the N-substituted glucamine employed) or in catalytic amounts (concentrations which are markedly below the chosen concentration of N-substituted glucamine). If, when using catalytic amounts, it is to be ensured that the process according to the invention is carried out approximately quantitatively, a system which continuously regenerates the reactant which is present only in a catalytic amount must also be added to the reaction mixture. This system can be, for example, an enzyme which ensures reoxidation (in the presence of oxygen or other oxidizing agents) of an electron acceptor which is reduced in the course of the reaction according to the invention.

If nutrient media is used with intact microorganisms in a growing culture, nutrient media can be solid, semi-solid or liquid. Aqueous-liquid nutrient media are preferably employed when media is used. Suitable media and suitable conditions for cultivation include known media and known conditions to which N-substituted glucamine or salts thereof can be added.

The N-substituted glucamine or salts thereof to be oxidized in the process according to the invention can be added to the base nutrient medium either on its own or as a mixture with one or more oxidizable compounds. Additional oxidizable compounds which can be used include polyols, such as sorbitol or glycerol.

If one or more oxidizable compounds are added to the nutrient solution, the N-substituted glucamine or salts thereof to be oxidized can be added either prior to inoculation or at any desired subsequent time (between the early log phase and the late stationary growth phase). In such a case the oxidizing organism is pre-cultured with the oxidizable compounds. The inoculation of the nutrient media is effected by a variety of methods including slanted tube cultures and flask cultures.

Contamination of the reaction solution should be avoided. To avoid contamination, sterilization of the nutrient media, sterilization of the reaction vessels and sterilization of the air required for aeration should be undertaken. It is possible to use, for example, steam sterilization or dry sterilization for sterilization of the reaction vessels. The air and the nutrient media can likewise be sterilized by steam or by filtration. Heat sterilization of the reaction solution containing the substrates (N-substituted glucamine) is also possible.

The process of the invention can be carried out under aerobic conditions using shake flasks or aerated and agitated tanks. Preferably, the process is carried out by the aerobic submersion procedure in tanks, for example in conventional fermentors. It is possible to carry out the process continuously or with batch or fed batch modes, preferably the batch mode.

It is advantageous to ensure that the microorganisms are adequately brought into contact with oxygen and the N-substituted glucamines. This can be effected by several methods including shaking, stirring and aerating.

If foam occurs in an undesired amount during the process, chemical foam control agents, such as liquid fats and oils, oil-in-water emulsions, paraffins, higher alcohols (such as octadecanol), silicone oils, polyoxyethylene compounds and polyoxypropylene compounds, can be added. Foam can also be suppressed or eliminated with the aid of mechanical devices.

The time-dependent formation of 6-(substituted amino)-6-deoxy-α-L-sorbofuranose in the culture medium can be followed either by thin layer chromatography, HPLC, or with the aid of the increase in the inhibitory activity in the saccharase inhibition test. Preferably the time-dependent formation of 6-(substituted amino)-6-deoxy-α-L-sorbose is measured by HPLC.

The 6-(substituted amino)-6-deoxy-α-L-sorbofuranose obtained in accordance with the process of the invention is isolated from the reaction solution as follows: The cell mass is filtered off or centrifuged off and the supernatant liquor is passed through a column containing acid ion exchanger and rinsed with an alcohol or water. Elution is then carried out with a base and the eluate concentrated. After adding acetone or the like, the 6-(substituted amino)-6-deoxy-α-L-sorbose crystallizes out. If it is intended to carry out further processing of 6-(substituted amino)-6-deoxy-α-L-sorbose to N-substituted-1-deoxynojirimycin, isolation is not necessary. For producing N-substituted-1-deoxynojirimycin from 6-(substituted amino)-6-deoxy-α-L-sorbofuranose, the clear solution, after removal of the cell mass, is reduced, preferably in the presence of a catalyst.

This aspect of the invention (no isolation necessary) is particularly advantageous because the process proceeds directly from the supernatant liquor resulting from the removal of cell mass of the microbial oxidation reaction solution. Likewise, it is especially advantageous because, unlike prior art processes, no amino protecting group has to be removed. The process of the invention eliminates the need to make and isolate protecting group intermediates and avoids removal of the protecting group to obtain the desired compound. The elimination of these steps results in a more efficient process with greater conversions and overall yields. The 6-(substituted amino)-6-deoxy-α-L-sorbofuranoses also exhibit higher solubility, thus higher concentrations are obtainable, which results in high productivity and higher rates. In addition, the 6-(substituted amino)-6-deoxy-α-L-sorbofuranoses have great stability which impedes degradation and resulting byproducts.

Several known means are available for reduction (see for example P. N. Rylander, *Hydrogenation Methods* (Academic Press, (1985) pp 82–93 and *Organic Chemistry*, 3rd edition, Eds James B. Hendrickson, Donald J. Cram, George S. Hammond (McGraw-Hill, Chapter 18, 1970)). These means include metal hydride reduction, catalytic hydrogenation, dissolving metal reduction and electrochemical reduction. In general, to reduce 6-(substituted amino)-6-deoxy-α-L-sorbofuranose to N-substituted-1-deoxynojirimycin, 6-(substituted amino)-6-deoxy-α-L-sorbofuranose is charged to a flask followed by addition of decolorizing carbon. The stirred mixture is then filtered to remove the carbon. The filtrate is added to a hydrogenation apparatus, such as a Parr Laboratory Reactor, containing a hydrogenation catalyst. Catalyst loading from about 1–50% by weight of sorbofuranose using Group VIII B metals are used. Preferably about 10–30% is used. Such catalysts include but are not limited to palladium, platinum, nickel and rhodium. Supports for the catalysts may include but are not limited to alumina, barium sulfate, calcium carbonate, carbon, silica and kieselguhr. Typically, the support would contain a 1–20% metal loading, preferably a 4–10% loading. A palladium catalyst is preferred. However, the preferred catalyst for 6-phenylmethylamino-6-deoxy-α-L-sorbofuranose is platinum or Raney nickel. The mixture is hydrogenated for about 5 hours. Hydrogen pressure from about 1 to 100 atm can be used; preferably a range from about 1–5 atm is used. The catalyst is then removed and acid ion-exchange resin added to the filtrate to adsorb the N-substituted-1-deoxynojirimycin. The N-substituted-1-deoxynojirimycin is released from the resin and isolated.

Examples of N-substituted-1-deoxynojirimycins that can be produced by hydrogenating the 6-(substituted amino)-6-deoxy-α-L-sorbofuranose produced by the microbial oxidation process of the invention are:

N-methyl-1-deoxynojirimycin,
N-ethyl-1-deoxynojirimycin,
N-n-propyl-1-deoxynojirimycin,
N-1-methylethyl-1-deoxynojirimycin,
N-n-butyl-1-deoxynojirimycin,
N-1-methylpropyl-1-deoxynojirimycin,
N-1,1-dimethylethyl-1-deoxynojirimycin,
N-n-pentyl-1-deoxynojirimycin,
N-3-methylbutyl-1-deoxynojirimycin,
N-1-methylbutyl-1-deoxynojirimycin,
N-2-methylbutyl-1-deoxynojirmycin,
N-n-hexyl-1-deoxynojirimycin,
N-n-hepty-1-deoxynojirimycin,
N-n-octyl-1-deoxynojirimycin,
N-n-nonyl-1-deoxynojirimycin,
N-n-decyl-1-deoxynojirimycin,
N-(2-hydroxyethyl)-1-deoxynojirimycin,
N-(3-hydroxypropyl)-1-deoxynojirimycin,
N-(4- hydroxybutyl)-1-deoxynojirimycin,
N-(5-hydroxypentyl)-1-deoxynojirimycin,
N-(6-hydroxyhexyl)-1-deoxynojirimycin,
N-(7-hydroxheptyl)-1-deoxynojirimycin,
N-(8-hydroxyoctyl)-1-deoxynojirimycin,
N-(9-hydroxynonyl)-1-deoxynojirimycin,
N-(10-hydroxydecyl)-1-deoxynojirimycin,
N-(carboxymethyl)-1-deoxynojirimycin,
N-(2-carboxyethyl)-1-deoxynojirimycin,
N-(3-carboxypropyl)-1-deoxynojirimycin,
N-(4-carboxybutyl)-1-deoxynojirimycin,
N-(5-carboxypentyl)-1-deoxynojirimycin,
N-(6-carboxyhexyl)-1 -deoxynojirimycin,
N-(7-carboxyheptyl)-1-deoxynojirimycin,
N-(8-carboxyoctyl)-1-deoxynojirimycin,
N-(9-carboxynonyl)-1-deoxynojirimycin,
N-(10-carboxydecyl)-1-deoxynojirimycin,
N-phenyl-1-deoxynojirimycin,
N-(phenylmethyl)-1-deoxynojirimycin,
N-(2-phenyl ethyl)-1-deoxynojirimycin,
N-(3-phenyl propyl)-1-deoxynojirimycin,
N-(4-phenylbutyl)-1-deoxynojirimycin,
N-(5-phenylpentyl)-1-deoxynojirimycin, N-(6-phenylhexyl)-1-deoxynojirimycin, N-(7-phenylheptyl)-1-deoxynojirimycin, N-(8-phenyloctyl)-1-deoxynojirimycin, N-(9-phenylnonyl)-1-deoxynojirimycin, and N-(10-phenyldecyl)-1-deoxynojirimycin.

The following examples illustrate embodiments of the invention described herein. As would be apparent to skilled artisans, various changes and modifications are possible and are contemplated within the scope of the invention described.

DESCRIPTION OF THE PREFERRED EMBODIMENTS

Preparation of Cell Paste of Oxidizing Microorganisms

A *Gluconobacter oxydans* cell paste is prepared by inoculating a series of 10 liter fermentors, each containing eight liters of media with 60 gm./liter D-sorbitol, 24 gm./liter yeast extract, 48 gm./liter potassium phosphate dibasic and 0.3 ml./liter antifoam (Ucon LB 625) with the microorganism *G. oxydans* (DSM2003). The fermentors are agitated and aerated while controlling temperature (30° C.) and pH (5.5 to 6.5) during the cell growth period. The fermentations are terminated after about 27 hours when optical density measurements indicate the log growth phase has been completed. The broths are then cooled, centrifuged, and the cells resuspended in water (or 0.02M MgSO4) and centrifuged to produce washed cell paste. These cell pastes are subdivided into aliquots and stored at or below 10° C. until thawed for addition to a reaction solution.

The reaction solution can also be sterilized by autoclaving, as described below. A 5% (weight/volume) solution of N-butylglucamine containing 20 mM MgSO4, at pH 5.0, was autoclaved in a 500 ml shake flask with a silicon closure in place. The conditions for autoclaving were 121° C., 30 P.S.I., for 30 minutes. The pH was checked afterwards and found to be 5.0 at room temperature. There was no visible change in the color or the clarity of the solution, an indication that no caramelization or precipitation had occurred. Anaylsis by HPLC assay also showed that the reaction solutions before and after autoclaving were the same. *Gluconobacter oxydans* cells were added to the shake flask and HPLC results showed conversion of at least 90% after 48 hours. Controls (not autoclaved) indicated at least 90% conversion at 48 hours, also. Autoclaving can therefore be used as a method for sterilizing the reaction solution.

EXAMPLE 1

A 2.3-L Parr shaker bottle is charged with 1L of 3A ethanol and 83g (1.1 mol) of n-butylamine. The mixture is stirred and cooled while 16 mL of 12N hydrochloric acid is slowly added. The pH after this addition is 10. To the 2.3-L Parr bottle is added 200g (1.1 mol) of n-glucose followed by 60 g of 4% palladium-on-carbon (50% water-wet). The mixture is agitated rapidly and hydrogenated at a constant pressure of 4 arm of hydrogen at 60°±5° C. until the reaction is complete (as indicated by hydrogen uptake). The hydrogen is vented and the 4% palladium-on-carbon is removed by filtration through a layer of powdered cellulose. The catalyst is washed with 100 mL of 3A ethanol followed by 50 mL of water. The wash is combined with the filtrate to give a solution containing a mixture of N-butyl glucamine and the corresponding hydrochloride salt. The mixture is stirred and cooled while 80 mL of 12N hydrochloric acid is slowly added. The pH after this addition is 2.5. The ethanol is removed by distillation under reduced pressure. The residue contains approximately 270 g of N-n-butyl glucamine hydrochloride. The residue is diluted to 500 mL with water to produce a bulk solution of N-n-butyl glucamine hydrochloride which is used in the next step without purification.

EXAMPLE 2

A reaction solution is prepared by adding 109 ml of a bulk solution of N-n-butylglucamine hydrochloride (prepared in Example 1) with a concentration of 500 gm/L by HPLC to 460 ml of water in a 1-L bioreactor. The solution is adjusted to pH 5 by adding dilute sodium hydroxide and cooled to about 15° C. A total of 30 gm (wet weight) of washed *G. oxydans* cell paste is added and the reaction mixture is agitated (500 rpm) and aerated (0.5 vvm) while controlling the temperature at 15° C. and pH at 5. After 23 hours, the HPLC assay indicates that over 99% of the substrate has been converted for a 80% yield of 6-n-butylamino-6-deoxy-α-L-sorbo-furanose hydrochloride.

EXAMPLE 3

A flask is charged with 490 ml of bulk solution from the previous reaction (Example 2) which contains 6-(n-butylamino)-6-deoxy-α-L-sorbofuranose hydrochloride. The flask is charged with 5 g of activated decolorizing carbon. The mixture is stirred for 10 minutes at 25°±5° C. The carbon is removed by filtration through a layer of diatomaceous earth. The carbon is washed with approximately 25 ml of water, and the wash is combined with the filtrate.

A flask is charged with 8.4 g of 4% palladium-on-carbon (50% water-wet) and the filtrate from the carbon treatment. This mixture is stirred rapidly and hydrogenated at a constant pressure of hydrogen at 60 psig at 25°±5° C. until the reaction is complete as indicated by hydrogen uptake. The hydrogen is vented and a nitrogen atmosphere is applied to the reaction vessel. The palladium-on-carbon is removed by filtration through a layer of powdered cellulose. The catalyst is washed with 50 ml of water, and the wash is combined with the filtrate to give a solution containing N-n-butyl-1-deoxynojirimycin hydrochloride, as determined by HPLC analysis.

A flask is charged with 200 ml of sulfonic acid cation-exchange resin (water-wet) and the filtrate from the previous step containing N-n-butyl-1-deoxynojirimycin hydrochloride. The mixture is stirred slowly for 15 minutes at 25°±5° C., and the resin is removed by filtration. The resin is washed with approximately 100 ml of water, and the wash is combined with the filtrate. The flask is charged with another 100 ml of sulfonic acid cation-exchange resin (water-wet) and the filtrate. The mixture is stirred slowly for 15 minutes at 25°±5° C., and the resin is removed by filtration. The resin is washed with approximately 50 ml of water, and the wash is combined with the filtrate. The flask is charged with another 100 ml of sulfonic add cation-exchange resin (water-wet) and the filtrate from above. The mixture is stirred slowly for 15 minutes at 25°±5° C., and the resin is removed by filtration. The resin is washed with approximately 50 ml of water, and the wash is combined with the filtrate.

The sulfonic add cation-exchange resin portions are combined and charged to the filter and washed with 200 ml of methanol.

A flask is charged with the above methanol-washed sulfonic acid cation-exchange resin containing N-n-butyl-1-deoxynojirinycin, 500 ml of methanol and 65 ml of 14.8N ammonium hydroxide. The mixture is slowly stirred for 15 minutes, and the resin is removed by filtration. The resin is washed with 100 ml of methanol, and the wash is combined with the filtrate. The sulfonic acid cation-exchange resin is removed from the filter and is charged to the flask. The flask is charged with 500 ml of methanol and 65 ml of 14.8N ammonium hydroxide. The mixture is slowly stirred for 15 minutes, and the resin is removed by filtration. The resin is washed with 100 ml of methanol, and the Wash is combined with the filtrate. The sulfonic add cation-exchange resin is removed from the filter and is again charged to the flask. The flask is charged with 100 ml of methanol and 65 ml of 14.8N ammonium hydroxide. The mixture is slowly stirred for 15 minutes, and the resin is removed by filtration. The resin is washed with 100 ml of methanol, and the wash is combined with the filtrate.

The filtrates are combined, and the solvent is removed by distillation under reduced pressure. The residual water is removed by azeotropic distillation with approximately 200 ml of isopropyl alcohol under reduced pressure. The residue is suspended in a solution of 240 ml of acetone and 15 ml of methanol and the mixture is refluxed for 15 minutes. The mixture is cooled to 25°±2° C. The crude product is collected by filtration and washed with 25 ml of a cold 10:1 solution of acetone:methanol. The crude product is stirred with 150 ml of methanol and 13.5 g of activated decolorizing carbon and heated to 40°±5° C. for 1 hour. The activated decolorizing carbon is removed by filtration and washed with 100 ml of methanol. The methanol wash is combined with the filtrate and is concentrated to near dryness by distillation under reduced pressure. The flask is charged with 21 ml of methanol and heated to reflux. While maintaining reflux, 160 ml of ethyl acetate is added. The resulting mixture is cooled to 5°±2° C. for 14–18 hours. The product is collected by filtration and washed with 20 ml of a cold 8:1 solution of ethyl acetate:methanol. The product is dried in a vacuum oven for 20 hours at 35°±5° C. to give 23.7 g (45% of theory based on glucose) of N-n-butyl-1-deoxynojirimycin. Purity of this material by HPLC and derivitized GC was 99.8%. The structure was confirmed by NMR and IR.

This product is stored at ambient temperature under an atmosphere of argon in double polyethylene bags.

EXAMPLE 4

The microorganism *Gluconobacter oxydans* (DSM 2003, Federal Republic of Germany) is grown in two 10 liter fermentors each containing eight liters of media having 624 gm. D-sorbitol, 200 gm. yeast extract, 50 gm. potassium phosphate dibasic, 50 gm. glutamine and 2.5 ml. antifoam (Ucon LB 625, a polyalkylene glycol, Union Carbide Co., Danbury, Conn.). These fermentors are agitated and aerated while controlling temperature (about 30° C.) and pH (about 5.5 to 6.3) during the cell growth phase. The fermentation is terminated after about 27 hours (when optical density measure-merits indicate that the cell log growth has been completed). The two fermentation broths are harvested, pooled, and the cells recovered by centrifugation. After decanting the supernatant, the cells are resuspended in water and centrifuged to produce washed cells for the microbial oxidation reaction. The washed cells are stored at about 4° C. for several days. The cells are then immobilized by adding a portion of the cells to a solution of Gelrite gellan gum (0.6 gm. per 50 ml. water) at about 55° C. (Gelrite gellan gum is a polysaccharide comprising uronic, rhamnose and glucose, available from Kelco Co., San Diego, Calif.). This suspension is added dropwise to a room temperature solution of 0.2M MgSO4 to produce beads containing the immobilized cells. Beads containing the immobilized cells are recovered by filtration and stored at about 4° C. A portion of the beads containing the immobilized cells are added to 50 ml. of an aqueous solution containing 0.5 gm. N-n-butyl glucamine adjusted to about pH 6.1 (with oxalic acid). This reaction solution is transferred to a 250 ml. shake flask for incubation in a 30° C. shaker. The reaction solution is incubated for about four (4) days at 30° C., after which a new spot is detected by thin layer chromatography (TLC) assay as the desired reaction product 6-n-butylamino-6-deoxy-α-L-sorbofuranose.

EXAMPLE 5

A reaction solution is prepared by dissolving 3.0 gm. of N-n-butyl-glucamine in 120 milliliter of water, adjusting the solution to about pH 5.7 with concentrated hydrochloric acid, adding 0.36 gm. of anhydrous magnesium sulfate, adjusting the final solution to pH 5.0 (with concentrated hydrochloric acid) and then diluting with water to a final volume of 150 ml. with a final concentration of 20 gm./liter. After filtering through a 0.2 micron filter, 50 ml. of the solution is added to a 500 ml. shake flask along with 2 gm. wet cell paste of *G. oxydans*, prepared as described above in Example 4. The mixture is incubated in a shake flask at room temperature (about 23° C.) for 72 hours (while sampling periodically). The reaction is monitored with ion pairing reverse phase high performance liquid chromatography (HPLC) assay which shows conversion of N-n-butylglucamine to 6-n-butylamino-6-deoxy-α-L-sorbofuranose of 47%, 77% and 79% after 24, 48 and 72 hours, respectively.

EXAMPLE 6

A reaction solution is prepared by dissolving 10 gm. of N-n-butylglucamine in water which is then adjusted to pH 5 (with concentrated hydrochloric add) and 0.02M MgSO4. The solution is diluted to 200 ml. with water and filtered, yielding a final solution at pH 5.1 containing 50 gm./liter N-n-butylglucamine. This solution along with *G. oxydans* cell paste are transferred to a 250 ml. agitated reactor which is maintained at 20° C. in a water bath. The solution is incubated for three (3) days while agitating and maintaining the solution at about 20° C. Ion pairing reverse phase HPLC assay of the reaction solution (after 64 hours) indicates conversion of N-n-butylglucamine to 6-n-butylamino-6-deoxy-α-L-sorbofuranose of 90%.

EXAMPLE 7

Four 50 mL samples of N-n-butylglucamine at 50 grams per liter, pH 5.0, 20 mM magnesium sulfate are treated with *G. oxydans* in shake flasks at room temperature. After three days, essentially all of the N-n-butylglucamine has been converted to 6-n-butylamino-6-deoxy-α-L-sorbofuranose by HPLC assay.

6-n-butylamino-6-deoxy-α-L-sorbofuranose is purified as follows. After centrifuging to remove cells, the clear, amber supernatant is treated with charcoal (2 grams in 167 mL) to decolorize. To this filtrate is added 3 grams of Amberlite (Robin and Haas) 200 resin (previously treated with concentrated HCl and water washed to convert it to the acid form), allowing 45 minutes for equilibration to remove inorganic cations. After removing the Amberlite resin, the pH, which has decreased to about 2 from 4.4, is adjusted with aliquots of Pharmacia Q-Sepharose (previously converted to the hydroxide form by repeated suspensions in 2.5 N NaOH) until the pH reaches 4.7. A total of 23 grams of wet Q-Sepharose is added to remove sulfate and chloride anions. This slightly off-white filtrate is aliquoted into 50 mL serum bottles, frozen at −50° C. overnight, then dried at shelf temperatures of −20° C. for three days, 0° C. for 24 hours and 20° C. for 2 hours. The dried vials are capped with silicone stoppers, capped and stored at −20° C. The dried solids were characterized by NMR and IR to confirm structure. Purity was confirmed by moisture analysis, HPLC and ion chromatography.

EXAMPLE 8

The microorganism, *Corynebacterium betea* (ATCC 13437) also known as *Curtobacterium flaccumfaciens* (DSM20141), is grown by inoculating 300 ml of autoclaved nutrient solution containing 10 g/l tryptone, 5 g/l yeast extract, and 5 g/l sorbitol with a 0.5 ml aliquot of culture from a stock vial. This solution is transferred to a sterile 2.8 shake flask together with 0.3 ml of antifoam (such as UCON LB625). The flask is inserted on a shaker which is agitated at 200 rpm while maintaining the temperature at 25° C. After 24 hours incubation, the cells (which are in the late log phase based on optical density) are harvested aseptically by centrifugation. The cells are transferred to a 250 ml non-baffled shake flask containing 50 ml of autoclaved nutrient solution (as above) in which 1 g of N-n-butylglucamine has been dissolved. This solution containing the N-n-butylglucamine is at a pH of about 8. The shake flask is incubated at 25° C. on a shaker which is agitated at 200 rpm for 48 hours. The HPLC assay indicates that about 3% of the N-n-butylglucamine is converted to 6-n-butylamino-6-deoxy-α-L-sorbofuranose.

EXAMPLE 9

N-n-butylglucamine is dissolved in water and the pH adjusted to 5.0 with hydrochloric acid and magnesium sulfate added to 20 mM, giving a final concentration of N-n-butylglucamine of 5 grams per liter. To 50 mL of this solution (in an autoclaved 500 mL shake flask) are added 2 grams (wet cell weight) of washed *G. oxydans* cells and the suspension rotated at 120 rpm at room temperature. After 24 hours, 37% of the initial charge of N-n-butylglucamine has been converted to 6-n-butylamino-6-deoxy-α-L-sorbofuranose.

EXAMPLE 10

N-n-butylglucamine is dissolved in water to give a final concentration of 20 gm/L after pH adjustment to 5.0 (with hydrochloric acid) and adding magnesium sulfate to 20 mM. To 50 mL of this solution (in an autoclaved 500 mL shake flask) are added 2 grams (wet weight) washed *G. oxydans* cells and the suspension placed at 30° and rotated at 200 rpm. After 24 hours 47% of the initial charge of N-n-butylglucamine has been converted to 6-n-butylamino-6-deoxy-α-L-sorbofuranose (by HPLC assay). After 48 hours, 81% has been converted to 6-n-butylamino-6-deoxy-α-L-sorbofuranose.

EXAMPLE 11

20 grams of N-n-butylglucamine are suspended in 156 mL water and 6 mL concentrated HCl added. Then 0.48 gm anhydrous magnesium sulfate is added and the pH adjusted to 5.0 (with sodium hydroxide). After adjusting the volume to 200 mL, the solution is filtered through a 0.2 μfilter and placed in a 250 mL spinner flask. The solution is aerated at 1 vvm with air, cooled to 5° C. and 8.7 grams (wet weight) of washed *G. oxydans* cells added. After 5 days 67% of the initial charge of N-n-butylglucamine has been converted to 6-n-butylamino-6-deoxy-α-L-sorbofuranose (by the HPLC assay).

EXAMPLE 12

The pH of 50 mL of 50 gm/L N-n-butylglucamine solution is adjusted to 3.5 (with hydrochloric acid), placed in a 500 mL shake flask and 5 grams of a 40% suspension of washed *G. oxydans* cells added. This is placed on a shaker at room temperature. After 24 hours 46% of the amino sugar is converted to 6-n-butylamino-6-deoxy-α-L-sorbofuranose by the HPLC assay.

EXAMPLE 13

In 305 grams of water 22 grams of N-n-butylglucamine is suspended and the pH adjusted to 7.0 (with hydrochloric acid). After adjusting the volume to 415 mL, 50 mL are aliquoted and 2.9 mL freshly thawed, and washed *G. oxydans* cells added. After 20 hours, 81% of the initial N-n-butylglucamine has been converted to 6-n-butylamino-6-deoxy-α-L-sorbofuranose as detected by HPLC assay.

EXAMPLE 14

2.5 Grams of N-n-butylglucamine suspended in 42 mL of water is titrated to pH 5 with nitric acid and the volume adjusted to 50 mL. This is filtered through a 0.2μfilter and placed in a shake flask. Washed *G. oxydans* cells are added. After 4 hours, 44% of the initial charge of N-n-butylglucamine has been converted to 6-n-butylamino-6-deoxy-α-L-sorbofuranose, and after 24 hours, conversion to product is over 90% (by HPLC assay).

EXAMPLE 15

N-n-butylglucamine is prepared in substantial accordance with the teaching of Example 14 except that sulfuric acid is used in place of nitric acid. After 4 hours, HPLC assay indictes conversion of 7% of the initial charge of N-n-butylglucamine to 6-n-butylamino-6-deoxy-α-L-sorbofuranose and after 24 hours, conversion increased to 32%.

EXAMPLE 16

N-n-butylglucamine is prepared in substantial accordance with the teaching of Example 14 except that acetic add is used in place of nitric add. After 4 hours, 20% of the initial charge of N-n-butylglucamine is converted to 6-n-butylamino-6-deoxy-α-L-sorbofuranose and after 24 hours, 35% of the initial charge is detected as 6-n-butylamino-6-deoxy-α-L-sorbofuranose.

EXAMPLE 17

N-n-butylglucamine is prepared in substantial accordance with the teaching of Example 14 except that phosphoric acid is used in place of nitric acid. After 4 hours, HPLC detected conversion of 21% of the initial charge of N-n-butylglucamine to 6-n-butylamino-6-deoxy-α-L-sorbofuranose and 44% after 24 hours.

EXAMPLE 18

Ten grams of N-n-butylglucamine is suspended in 160 mL water plus 8 mL 0.5M magnesium sulfate, then titrated to pH 5.0 with hydrochloric acid and diluted to 200 mL. Of this solution, 50 mL is then autoclaved for 30 minutes at 121° C., cooled to room temperature and placed in a shake flask. 24 Hours after addition of *G. oxydans* cells, 57% of the initial charge of N-n-butylglucamine has been converted to 6-n-butylamino-6-deoxy-α-L-sorbofuranose.

EXAMPLE 19

*Gluconobacter oxydans* (DSM 2003) is grown in shake flasks under standard conditions, 5% sorbitol, 2% yeast extract, 3 grams per liter succinic acid, pH 6.3, at 30° C. (see S. A. White and G. W. Claus (1982), J. Bacteriology 150:934–943 and Noel R. Krieg ed., Bergey's Manual of Systematic Bacteriology, Vol. 1, Williams & Wilkins, Baltimore/London, p.275; c. 1984). Cells are isolated by centrifugation and washed with 20 mM magnesium sulfate (at 2° C.). To 50 mL of N-n-butylglucamine (pH 5.0 with hydrochloric acid) are added 2 grams of packed wet cells, and this suspension is agitated at 120 rpm, at room temperature, for 24 hours. After 24 hours, HPLC analysis indicates that 38% of the initial charge of N-n-butylglucamine has been converted to 6-n-butylamino-6-deoxy-α-L-sorbofuranose.

EXAMPLE 20

*Gluconobacter oxydans* (ATCC 621) is grown and converts N-n-butylglucamine in substantial accordance with the teaching of Example 6, except 51% of the initial N-n-butylglucamine is converted to 6-n-butylamino-6-deoxy-α-L-sorbofuranose.

EXAMPLE 21

A reaction solution is prepared by adding 91 gm N-n-butylglucamine to 580 ml of water in a 1-L bioreactor. The suspension is adjusted to about pH 5 (with concentrated HCl) and cooled to about 15° C. A total of 24 gm (wet weight) of washed *G. oxydans* cell paste is added and the reaction mixture is agitated (500 rpm) and aerated (0.5 vvm) while controlling the temperature at 15° C. and pH at 5. After 23 hours, the HPLC assay indicates that over 99% of the substrate has been converted for a 83% yield of 6-n-butylamino-6-deoxy-α-L-sorbofuranose.

EXAMPLE 22

A reaction solution is prepared by adding 750 gm N-n-butylglucamine to 7.2 L of water in a 10-L bioreactor. The suspension is adjusted to pH 5 (with concentrated HCl) and cooled to about 15° C. A total of 300 gm (wet weight) of washed *G. oxydans* cell paste is added and the reaction mixture is agitated (350–500 rpm) and aerated (0.4 vvm) while controlling the temperature at 15° C. and pH at 5. After 14 hours, the HPLC assay indicates that over 97% of the substrate has converted for a 85% yield of 6-n-butylamino-6-deoxy-α-L-sorbofuranose.

EXAMPLE 23

A reaction solution is prepared by adding 46 gm N-n-butylglucamine to 620 ml of water in a 1-L bioreactor. The suspension is adjusted to pH 5 (with concentrated hydrochloric acid) and cooled to about 15° C. A total of 30 gm (wet weight) of washed *G. oxydans* cell paste is added and the reaction mixture is agitated (350 rpm) and aerated (0.2 vvm) while controlling the temperature at 15° C. and pH at 5. After 77 hours, the HPLC assay indicates that over 97% of the substrate has been converted for a 75% yield of 6-n-butylamino-6-deoxy-α-L-sorbofuranose.

EXAMPLE 24

A reaction solution is prepared by adding 81 gm N-n-butylglucamine hydrochloride to 640 ml of water in a 1-L bioreactor. The solution, which is pH 5, is cooled to about 15° C. A total of 70 gm (wet weight) of washed *G. oxydans* cell paste is added and the reaction mixture is agitated (400 rmp) and aerated (0.5 vvm) while controlling the temperature at 15° C. and pH at 5. After 20 hours, the HPLC assay indicates that over 99% of the N-n-butylglucamine has been converted for a 80% yield of 6-n-butylamino-6-deoxy-α-L-sorbofuranose.

EXAMPLE 25

A reaction solution is is prepared by adding 170 ml of a bulk solution of N-n-butylglucamine hydrochloride with a concentration of 450 gm/L (by HPLC) to 210 ml of water in a 1-L bioreactor. The solution is adjusted to pH 5 by adding dilute sodium hydroxide and cooled to about 15° C. A total of 20 gm (wet weight) of washed *G. oxydans* cell paste is added and the reaction mixture is agitated (1000 rpm) and aerated (1 vvm) while controlling the temperature at 15° C. and pH at 5. After 27 hours, the HPLC assay indicates that over 97% of the substrate has been converted for a 80% yield of N-n-butylamino-6-deoxy-α-L-sorbofuranose.

EXAMPLE 26

1.0 gram of N-ethylglucamine is suspended in 50 mL water and titrated to pH 5.0 with concentrated HCl (simultaneously dissolving the aminosugar). This solution is placed in a 500 mL shaker flask. To this solution is added 2.0 grams (wet weight) of washed *Gluconobacter oxydans* cells and the solution agitated at 100–120 rpm. After 24 hours, HPLC analysis indicates that 70% of the initial charge of N-ethylglucamine has been converted to 6-ethylamino-6-deoxy-α-L-sorbofuranose, and after 48 hours, at least 90% has been converted. After 72 hours, the supernatant is separated from the cells and sterile filtered. An aliquot (10 mL) of the supernatant is adjusted to pH 9.0 with concentrated NH4OH, chilled in an ice bath, and 100 mg NaBH4 is added. After standing in the ice bath overnight, the samples are acetylated and assayed by gas chromatography (GC)-mass spectroscopy. GC-mass spectroscopy indicates a 60% yield of N-ethyl-1-deoxynojirimycin from 6-ethylamino-6-deoxy-α-L-sorbofuranose (Chemical ionization mass spectroscopy of the acetylated product indicates that the GC peak corresponding to the reduced cyclized product has a parent peak mass of 360 (M+H), corresponding to tetra-acetylated N-ethyl-1-deoxynojirimycin).

EXAMPLE 27

N-(2-hydroxyethyl)glucamine is microbially oxidized in substantial accordance with the teaching of Example 26, except N-(2-hydroxyethyl)glucamine is used in place of N-ethylglucamine and N-(2-hydroxyethyl)-1-deoxynojirimycin is obtained instead of N-ethyl-1-deoxynojirimycin. HPLC analysis after 24 hours indicates that 79% of the initial charge of N-(2-hydroxyethyl)glucamine has been converted to 6-(2-hydroxyethyl)amino-6-deoxy-α-L-sorbofuranose. After 48 hours, at least 90% of the initial charge has been converted. After 72 hours, the supernatant is separated from the cells and sterile filtered. The pH of an aliquot (10 mL) is adjusted to pH 9.0 with concentrated NH4OH, chilled in an ice bath, and 100 mg NaBH4 is added. After standing in the ice bath overnight, the samples are acetylated and assayed by gas chromatography mass spectroscopy (GC-MS). GC-MS indicates a 95% yield of N-(2-hydroxyethyl)-1-deoxynojirimycin from 6-(2-hydroxyethyl)amino-6-deoxy-α-L-sorbofuranose (chemical ionization mass spectroscopy of the acetylated product indicated the GC peak corresponding to the reduced, cyclized product has a parent peak mass of 418 (M+H) corresponding to the penta-acetylated N-2-hydroxyethyl-1-deoxynojirimycin.

EXAMPLE 28

N-phenylmethylglucamine is microbially oxidized in substantial accordance with the teaching of Example 26, except N-phenylmethylglucamine is used in place of N-ethylglucamine and N-phenylmethyl-1-deoxynojirimycin is obtained instead of N-ethyl-1-deoxynojirimycin. After 4 hours, HPLC analysis indicates that 48% of the initial charge of N-phenylmethylglucamine has been converted to 6-(phenylmethyl)amino-6-deoxy-α-L-sorbofuranose. After 24 hours, at least 90% of the initial charge has been converted. When reduced and acetylated in substantial accordance with the teaching of Example 26, GC-MS (chemical ionization) gave a parent peak (M+H) of 422 corresponding to the tetra-acetyl N-phenylmethyl-1-deoxynojirinycin. GC indicates a 98% yield of N-phenylmethyl-1-deoxynojirinycin from 6-(phenylmethyl)amino-6-deoxy-α-L-sorbofuranose.

EXAMPLE 29

N-n-octylglucamine is microbially oxidized in substantial accordance with the teaching of Example 26, except N-n-octylglucamine is used in place of N-ethylglucamine and N-n-octyl-1-deoxynojirimycin is obtained instead of N-ethyl-1-deoxynojirinycin. Due to the high affinity of the N-n-octylglucamine for the resins used to analyze the conversions, the HPLC assay is not used. Conversion is monitored by reduction with $NaBH_4$ at alkaline pH, acetylation, and GC-mass spectroscopy. When reduced and acetylated in substantial accordance with the teaching of Example 26, GC-MS (chemical ionization) gives a parent peak (M+H) of 444, corresponding to the tetra-acetyl N-octyl-1-deoxynojirimycin. GC-MS indicates a 94% yield of N-n-octyl-1-deoxynojirimycin from 6-n-octylamino-6-deoxy-α-L-sorbofuranose.

EXAMPLE 30

About 1500 mL of an aqueous solution which contains about 96 g (0.41 moles) of 6-n-butylomino-6-deoxy-α-L-sorbofuranose is charged to a 4 L Erlenmeyer flask followed by 13 g of decolorizing carbon. The mixture is stirred for about 10 minutes and the carbon removed by filtration. The filtrate is added to a 2.3 L Parr bottle which contains about 19 g (50% wet) 4% palladium-on-carbon. The mixture is hydrogenated for about 5 hours at 60 psig of hydrogen pressure and ambient temperature. After removal of the catalyst by filtration, 550 mL of Dowex® 50×8–200 ion-exchange resin (Dow Chemical, Midland, Mich.), a strong acid cationic exchange resin, with polystyrenedivinylbenzene backbone, is added to the filtrate. The slurry is stirred for 30 minutes and the resin, (which contains the product) is collected. The filtrate is retreated (as described above) with about 250 mL of Dowex resin. The two resin filter cakes are combined and the product released from the resin using about 2.5 L of $MeOH/NH_4OH$ (4:1). The extracts are concentrated and the water removed by azeotropic distillation. The residue is recrystallized from about 610 mL of methanol/acetone (1:16). The solids are dissolved in about 375 mL methanol and decolorized using about 7.6 g of decolorizing carbon. The filtrate is concentrated and the residue recrystallized from about 625 mL of methanol/ethyl acetate (1:9). The product is then dried.

Yield: 65 g =75% of theory
Melting Point: 132°–135° C.
Purity by Derivitized GC Assay: 99.5%

EXAMPLE 31

Several reaction solutions such as those prepared in Examples 5, 6 and 7, are centrifuged, pooled and filtered to produce a clarified solution for conversion to N-n-butyl-1-deoxynojirimycin. About 100 ml of this clear, but colored solution is first treated with activated charcoal and then transferred to a Parr Laboratory Reactor (Baxter Healthcare Corp., Scientific Products Division, McGaw, Ill.) to which is also added palladium/carbon catalyst. The system is operated at room temperature with 50 psig hydrogen for about 2.5 hours after which the catalyst is filtered off to prepare a filtrate for further purification. The filtrate is contacted with a strong acid cationic resin (Dowex 50×8–200 mesh) to adsorb the product (N-butyl-1-deoxynojirimycin) which is eluted with a methanol: ammonium hydroxide (3:1) solution. This solution is concentrated to a thick oil by evaporation after which a mixture of methanol: acetone (1:16) is added to crystallize the product. The isolated material is identified as N-n-butyl-1-deoxynojirimycin with a 99.5% purity by gas chromatography (GC) assay for a 53% isolated yield of N-n-butyl-1-deoxynojirimycin.

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included therein.

What is claimed is:

1. A process which comprises aminating D-glucose to an N-substituted glucamine of the formula:

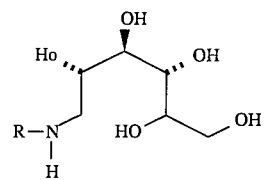

or salts thereof, wherein R is phenyl, $C_1$–$C_{10}$ alkyl, $C_1$–$C_{10}$ alkyl substituted with phenyl or carboxyl, or $C_2$–$C_{10}$ alkyl substituted with hydroxy, oxidizing said N-substituted glucamine with a microorganism or extract thereof, which oxidizes said glucamine to produce a compound of the formula:

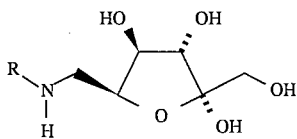

wherein R is as described above, and then reducing said compound to produce N-substituted-1-deoxynojirimycin of the formula:

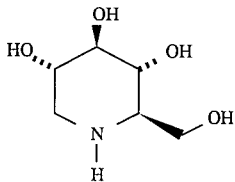

wherein R is as described above, and recovering the N-substituted-1-deoxynojirimycin.

2. The process of claim 1 in which the microorganism is of the order Pseudomonadales.

3. The process of claim 1 in which the microorganism is of the genus Gluconobacter.

4. The process of claim 2 in which the microorganism is *Gluconobacter oxydans*.

5. The process of claim 4 in which the microorganism is *Gluconobacter oxydans* subsp. *suboxydans*.

6. The process of claim 1 in which the microorganism is a Coryneform.

7. The process of claim 6 in which the microorganism is *Coryneform betea*.

8. The process of claim 1 in which D-glucose is aminated to N-n-butyl glucamine which in turn is oxidized to produce 6-n-butylamino-6-deoxy-α-L-sorbofuranose which is reduced to produce N-n-butyl-1-deoxynojirimycin.

9. The process of claim 1 in which D-glucose is aminated to N-(2-hydroxyethyl) glucamine which in turn is oxidized to produce 6-(2-hydroxyethyl)amino-6-deoxy-α-L-sorbofuranose which is then reduced to produce N-(2-hydroxyethyl)-1-deoxynojirimycin.

10. The process of claim 1 in which D-glucose is aminated to N-n-octyl glucamine which in turn is oxidized to produce 6-(n-octylamino)-6-deoxy-α-L-sorbofuranose which is reduced to produce N-n-octyl-1-deoxynojirimycin.

11. The process of claim 1 in which D-glucose is aminated to N-phenylmethyl glucamine which in turn is oxidized to produce 6-(phenylmethyl)amino-6-deoxy-α-L-sorbofuranose which is reduced to produce N-(phenylmethyl)1-deoxynojirimycin.

12. The process of claim 1 in which D-glucose is aminated to N-3-carboxypropyl glucamine which in turn is oxidized to produce 6-(3-carboxypropyl)amino-6-deoxy-α-L-sorbofuranose which is reduced to produce N-(3-carboxypropyl)-1-deoxynojirimycin.

13. The process of claim 1 in which D-glucose is aminated to N-phenylglucamine which in turn is oxidized to produce 6-phenylamino-6-deoxy-α-L-sorbofuranose which is reduced to produce N-phenyl-1-deoxynojirimycin.

14. The process of claim 1 in which D-glucose is aminated to N-ethyl glucamine which in turn is oxidized to produce 6-ethylamino-6-deoxy-α-L-sorbofuranose which is reduced to produce N-ethyl-1-deoxynojirimycin.

* * * * *

UNITED STATES PATENT AND TRADEMARK OFFICE
CERTIFICATE OF CORRECTION

PATENT NO. : 5,602,013
DATED : February 11, 1997
INVENTOR(S) : Roy W. Grabner et al.

It is certified that error appears in the above-identified patent and that said Letters Patent is hereby corrected as shown below:

Column 4:
Line 49, "N-substituted 1-amino-" should read --N-substituted=1-amino--

Column 5:
Line 30, "add" should read --acid--;

Column 12:
Line 59, "add" should read --acid--; and
Line 65, "add" should read --acid--.

Column 13:
Line 12, "Wash" should read --wash--; and
Line 13, "add" should read --acid--.

Column 14:
Line 40, "add" should read --acid--.

Column 16:
Line 2, "0.2 µfilter" should read --0.2 µ filter--;
Line 3, "acrated" should read --aerated--;
Line 32, "Grams" should read --grams--;
Line 34, "0.2µ filter" should read --0.2 µ filter--;
Line 46, "indictes" should read --indicates--;
Line 53, "add" should read --acid--; and
Line 54, "add." should read --acid.--.

Column 17:
Line 7, "Hours" should read --hours--.

Column 18:
Line 22, "is" (second occurrence) should be deleted.

UNITED STATES PATENT AND TRADEMARK OFFICE
CERTIFICATE OF CORRECTION

PATENT NO.    : 5,602,013
DATED         : February 11, 1997
INVENTOR(S)   : Roy W. Grabner et al.

It is certified that error appears in the above-identified patent and that said Letters Patent is hereby corrected as shown below:

Column 19:
Line 54, "6-n-butylomino-6-dioxy-α-L" should read --6-n-butylamino-6-deoxy-α-L--.

Column 21:
Line 5, " 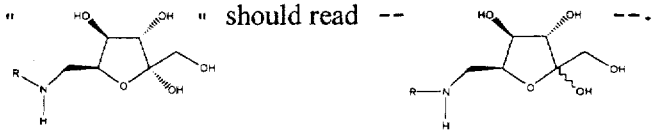 " should read -- 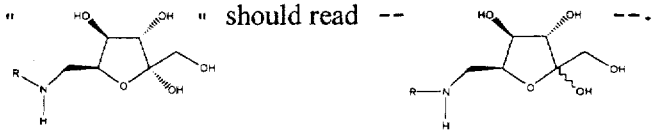 --.

Signed and Sealed this

Twenty-eighth Day of August, 2001

*Attest:*

*Attesting Officer*

NICHOLAS P. GODICI
*Acting Director of the United States Patent and Trademark Office*